United States Patent [19]
Kranz et al.

[11] Patent Number: 5,547,668
[45] Date of Patent: Aug. 20, 1996

[54] CONJUGATES OF FOLATE ANTI-EFFECTOR CELL ANTIBODIES

[75] Inventors: David M. Kranz, Champaign; Edward J. Roy; Todd A. Patrick, both of Urbana, all of Ill.

[73] Assignee: The Board of Trustees of The University of Illinois, Urbana, Ill.

[21] Appl. No.: 435,175

[22] Filed: May 5, 1995

[51] Int. Cl.$^6$ .................. A61K 39/395; C07K 16/28; C21P 21/08
[52] U.S. Cl. .................. 424/181.1; 424/154.1; 424/173.1; 424/178.1; 435/70.21; 435/172.2; 435/240.27; 530/391.7; 530/391.1; 530/388.75; 530/389.6
[58] Field of Search .................. 424/133.1, 134.1, 424/135.1, 136.1, 138.1, 139.1, 154.1, 155.1, 174.1, 173.1, 178.1, 182.1; 435/70.21, 172.2, 188, 240.27; 530/387.3, 387.7, 388.22, 388.7, 388.73, 388.75, 388.8, 388.85, 391.1, 391.3, 391.7, 389.6, 389.7

[56] References Cited

U.S. PATENT DOCUMENTS 5,030,719 7/1991 Umemoto et al. .................. 530/391
5,070,877 12/1991 Mohiuddin et al. .................. 128/653.4

(List continued on next page.)

OTHER PUBLICATIONS

Fanger et al (1990). Faseg J. 4(11) 2846–2849.
Leaman et al (1993) J. Biol. Chem. vol. 268 (33) 24847–24854.
Brigle, K. E., Spinella, M. J., Westin, E. H. & Goldman, I. D. [1994] *Biochem Pharmacol* 47:337–345.
Brigle, K. E., Seither, R. L., Westin, E. H. & Goldman, I. D. [1994] *Biol Chem* 269:4267–4272.
Brigle, K. E., Westin, E. H., Houghton, M. T. & Goldman, I. D. [1991] *J Biol Chem* 266:17243–17249.
Campell, I. G., Jones, T. A., Foulkes, W. D., & Trowsdale, J. [1991] *Cancer Res.* 51:5329–5338.
Fanger, Morganelli, & Guyre [1992] *Crit. Rev. Immunol.* 12:101–1240.
Haskins, K., Hannum, C., White, J., Rhoem, N., Kubo, R., Kappler, J. & Marrack, K. [1984] *J. Exp. Med.* 160:452–471.
Jansen, G., Westerhof, G. R., Kathmann, I., Rademaker, B. C., Rijksen, G., & Schornagel, J. H.[1989] *Cancer Res.* 49:2455–2459.
Kranz, D. M., Sherman, D. H., Sitkovsky, M. V., Pasternack, M. S. & Eisen, H. N. [1984] *Proc. Natl. Acad. Sci. USA* 81:573–577.
Kranz, D. M., Tonegawa, S. & Eisen, H. N. [1984] *Proc. Natl. Acad. Sci. USA* 81:7922–7926.
Leamon, C. P. & Low, P. S. [1992] *J Biol Chem* 267:24966–24971.
Leo, O., Foo, M., Sachs, D. H., Samelson, L. E. & Bluestone, J. A. [1987] *Proc. Natl. Acad. Sci. USA* 84:1374.
Miotti S., Canevari, S., Menard, S., Mezzanzanica, D., Porro, G., Pupa, S. M., Regazzoni, M., Tabliabue, E. & Colnaghi, M. I.[1987] *Int. J. Cancer* 39:297–303.

(List continued on next page.)

Primary Examiner—Robert D. Budens
Assistant Examiner—Julie E. Reeves
Attorney, Agent, or Firm—Dressler, Goldsmith, Shore & Milnamow, Ltd.

[57] ABSTRACT

The present invention provides a process of targeting folate-receptor-positive tumor cells for lysis by binding a conjugate of folate and an anti-T-cell-receptor antibody or an anti-Fc receptor antibody to those cells. A process of lysing folate-receptor-positive tumor cells comprising exposing the cells to a folate/anti-T-cell-receptor antibody in the presence of a population of T-cells is also provided. A process of lysing folate-receptor-positive tumor cells comprising exposing the cells to a folate/anti-Fc receptor antibody in the presence of a population of natural killer cells, monocytes, or macrophages is also provided. Still further, the present invention provides a conjugate of folate to an anti-T-cell-receptor antibody or an anti-Fc receptor antibody.

6 Claims, 10 Drawing Sheets

U.S. PATENT DOCUMENTS 5,108,921   4/1992   Low et al. .......................... 435/240.1
5,140,104   8/1992   Coughlin et al. ...................... 530/330

OTHER PUBLICATIONS

Ross et al., Cancer 73:2432, 1994.

Schodin, B. A. & Kranz, D. M. [1993] *J. Biol. Chem.* 268:25722–25727.

Soo Hoo, W. F. & Kranz, D. M. [1993] *J. Immunol.* 150:4331–4337.

Weitman et al., Cancer Research 52:3396, 1992.

Westerof, G. R., Jansen, G., Van Emmerik, N., Kathmann, I., Rijksen, G., Jackman, A. L. & Schornagel, J. H. et al. [1991] *Cancer Research* 51:5507–5513.

5,547,668

CONJUGATES OF FOLATE ANTI-EFFECTOR CELL ANTIBODIES

DESCRIPTION

1. Technical Field of the Invention

The field of the present invention is tumor cell lysis. More specifically, the field of the present invention is targeting folate-receptor-positive tumor cells for lysis. Tumor cells are targeted for lysis by binding to those cells an effective targeting amount of an anti-T-cell-receptor antibody, or other anti-effector cell antibody, conjugated to folate or a folate analogue.

2. Background of the Invention

High-affinity folate receptors (FR) with a $K_D$ of about 1 nM have recently been detected on the surface of a number of different types of human cancers. It has been estimated that 80% of ovarian tumors may express folate receptors. These receptors differ from the lower affinity reduced folate/methotrexate carrier ($K_D$ about 100 µM) that appears to be largely responsible for the transport of folate-based dihydrofolate reductase inhibitors such as methotrexate. The discovery of FR on tumor cells prompted recent searches for other anti-folate compounds that bind selectively to the FR; these include folate analogues that inhibit thymidylate synthesis.

Two mouse homologs of the human FR isoforms have been identified that bind folate with high affinity ($K_D$ about 1 nM). Two forms ($\alpha$ and $\beta$) of the mouse FR have been identified as 30 kDa lipid-linked membrane proteins. As in humans, FR also appear to be expressed at high levels on some mouse tumors. For example, mouse choroid plexus tumors that arise in SV40 transgenic mice express high levels of FR.

FRs have been used as targets for specific monoclonal antibodies such as MOv18 and MOv19. Targeting approaches with monoclonal anti-FR antibodies have included: $^{131}$I-labeled antibodies, engineering of constant regions to optimize antibody-dependent cellular cytotoxicity, and bispecific antibodies that target immune effector cells to tumor cells expressing the FR receptor (FR positive or FR$^+$ cells). The latter studies have used bispecific antibodies, anti-FR antibodies linked to either anti-Fc receptor antibodies or to anti-CD3 antibodies, for recruitment of monocyte/natural killer cells or cytotoxic T-cells, respectively. Clinical trials with the radiolabeled antibodies and the anti-FR/anti-CD3 bispecific antibodies have recently been initiated.

Another potential approach to targeting FR$^+$ tumor cells has relied on the ability of the FR to endocytose proteins that are covalently linked to folate. For example, tumor cells internalize momordin/folate conjugates and Pseudomonas exotoxin/folate conjugates. The protein/folate conjugates bound specifically to the FR and endocytosis resulted in delivery of the toxic moiety.

BRIEF SUMMARY OF THE INVENTION

The present invention provides that the conjugation or attachment of folate or an analogue thereof directly to an anti-T-cell-receptor antibody or other anti-effector cell antibody efficiently targets FR$^+$ tumor cells for lysis (see FIG. 1). These conjugates mediate lysis of mouse FR$^+$ tumors cells at very low concentrations (about 1 pM). In addition, tumor cell lines with a range of FR densities were killed while the parental line with no detectable FR was spared. The effectiveness is likely due in part to the finding that the binding affinity of the folate-linked antibody is nearly as high as free folate for the FR $\alpha$ and $\beta$ forms. The smaller size of the folate/anti-T-cell-receptor antibody conjugate as compared to bispecific antibodies that contain an anti-T-cell-receptor antibody coupled to an anti-FR antibody provides for therapeutic advantages.

In one aspect, the present invention provides a process of targeting folate-receptor-positive tumor cells for lysis. In accordance with that process, tumor cells are bound to an effective targeting amount of a conjugate of an anti-T-cell-receptor antibody conjugated to folate or an analogue thereof. Binding is accomplished by exposing the tumor cells to the conjugate and maintaining the cells under physiological conditions and for a period of time sufficient for binding to occur. Binding can only occur when the high affinity ligand, folate, is attached to the antibody. Any other high affinity analogues of folate work by the same principle when attached to the antibody.

The folate-receptor-positive tumor cells can be positive for either the previously identified $\alpha$- or the $\beta$-forms of the folate receptor, or presumably any form that has high affinity for folate. In a preferred embodiment, the anti-T-cell-receptor antibody is a monoclonal antibody. Preferably, the anti-T-cell-receptor antibody is an antibody directed against either the variable region of the receptor (as shown with monoclonal antibody KJ16) or against another receptor subunit, CD3 (as shown with monoclonal antibody 2C11).

In another aspect, the present invention provides a process of lysing folate-receptor-positive tumor cells comprising exposing the tumor cells to a population of T-cells in the presence of an effective targeting amount of a conjugate of an anti-T-cell-receptor antibody and folate or an analogue thereof and maintaining the cells for a period of time sufficient for lysis. Other types of normal immune effector cells, such as natural killer cells, are also effective at targeting folate receptor positive tumor cells in the presence of antibody/folate conjugates directed against their receptors (e.g., Fc receptors).

BRIEF DESCRIPTION OF THE DRAWINGS

In the drawings, which form a portion of the specification.

DETAILED DESCRIPTION OF THE INVENTION

I. The Invention

Figure 1:
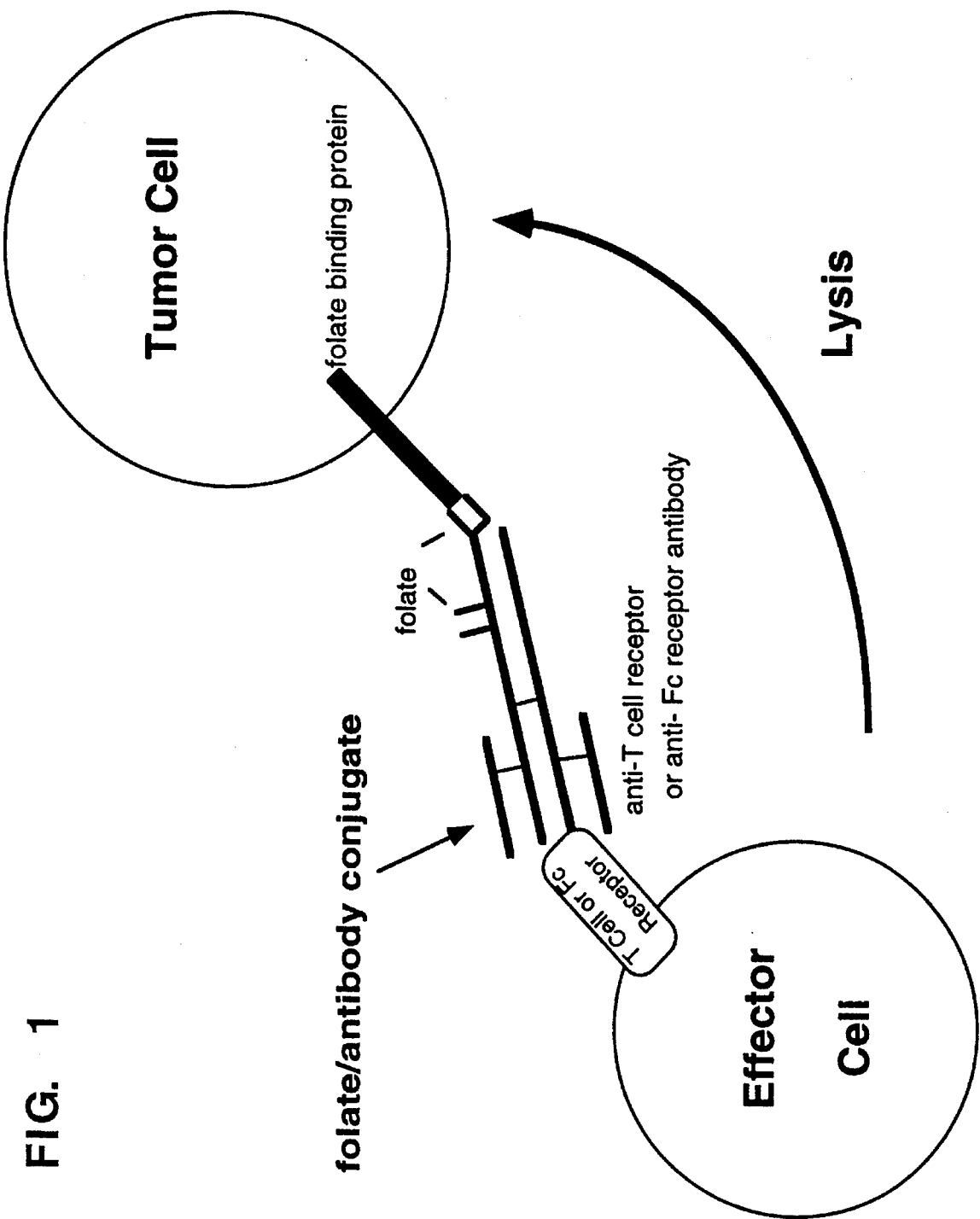
FIG. 1 shows the principle of action of the folate/antibody conjugates described in this application.

High-affinity folate receptors (FR) are expressed at elevated levels on many human tumors. For example, it has been estimated that 80% of ovarian tumors express FR (Miotti S., Canevari, S., Menard, S., Mezzanzanica, D., Porro, G., Pupa, S. M., Regazzoni, M., Tabliabue, E. & Colnaghi, M. I. [1987] *Int. J. Cancer* 39, 297–303). A common form of chemotherapy, with the folate analogue methotrexate (MTX), can lead to resistance to the drug: it has been proposed that the "escaping" tumor cells may express the FR in lieu of the typical folate transporter that also binds to MTX (i.e. the reduced folate/MTX carrier). Because FR does not bind to MTX with high affinity, these tumor cells can survive only by receiving folate through the FR (Westerof, G. R., Jansen, G., van Emmerik, N., Kathmann, I., Rijksen, G., Jackman, A. L. & Schornagel, J. H. et al. [1991] *Cancer Research* 51, 5507–5513). In this scenario it is thought that specific targeting of the FR may be a useful followup to chemotherapy with methotrexate.

Bispecific antibodies that bind the FR and the T-cell-receptor can mediate lysis of these tumor cells by cytotoxic T lymphocytes (CTLs). The present invention provides that conjugates of folate covalently linked to anti-T-cell-receptor antibodies mediate lysis of tumor cells that express either the α or β form of the FR. Intact antibodies with an average of 5 folates/molecule exhibited high affinity for FR$^+$ tumor cells but did not bind to FR$^-$ tumor cells. Lysis of FR$^+$ cell lines could be detected at concentrations as low as 1 pM (about 0.1 ng/ml), a concentration that is 1000 fold lower than the concentration required to detect binding to the FR$^+$ cells.

Various FR$^+$ mouse tumor cell lines were targeted with each of three different anti-T-cell-receptor antibodies that were tested as conjugates to folate. The antibodies included 1B2, a clonotypic antibody specific for the cytotoxic T-cell clone 2C, KJ16, an anti-Vβ8 antibody, and 2C11, an anti-CD3 antibody. These antibodies differ in affinities by up to 100-fold, yet the cytolytic capabilities of the folate/antibody conjugates differed by no more than ten-fold. The reduced size (in comparison with bispecific antibodies) and high affinity of folate conjugates make them useful as immunotherapeutic agents in targeting tumors that express folate receptors.

II. A Process of Targeting Tumor Cells for Lysis

In one aspect, the present invention provides a process of targeting a folate-receptor-positive (FR$^+$) tumor cell for lysis. In accordance with that process, a tumor cell is bound to an effective targeting amount of a conjugate of an anti-T-cell-receptor antibody and folate or an analogue thereof.

In a preferred embodiment, the anti-T-cell-receptor antibody is a monoclonal antibody. Preferably, the anti-T-cell-receptor antibody is specific for the T-cell-receptor variable regions (as with antibody KJ16 in the examples below) or the T-cell-receptor subunit, CD3 (as with antibody 2C11 in the examples below).

Binding is accomplished by exposing the tumor cell to an effective targeting amount of the anti-T-cell-receptor antibody/folate conjugate and maintaining the cell under physiological conditions and for a period of time sufficient for the conjugate to bind to the cell.

The folate-receptor-positive tumor cells can be positive for either the α- or the β-form of the folate receptor. Exemplary tumor cells that express either the α- or β-form of the FR include various human ovarian tumors and leukemia cell lines (Campell, I. G., Jones, T. A., Foulkes, W. D., & Trowsdale, J. [1991] *Cancer Res.* 51, 5329–5338; Miotti S., Canevari, S., Menard, S., Mezzanzanica, D., Porro, G., Pupa, S. M., Regazzoni, M., Tabliabue, E. & Colnaghi, M. I. [1987] *Int. J. Cancer* 39, 297–303; Jansen, G., Westerhof, G. R., Kathmann, I., Rademaker, B. C., Rijksen, G., & Schornagel, J. H. [1989] *Cancer Res.* 49, 2455–2459).

Folate is conjugated to an anti-T-cell-receptor antibody. An anti-T-cell-receptor antibody used in the present invention can be a polyclonal or monoclonal antibody. Anti-T-cell-receptor antibodies are well known in the art. Such antibodies can be obtained commercially from vendors, from deposits of hybridomas made in accordance with the terms of the Budapest Treaty, or they can prepared using standard techniques well known in the art. By way of example, monoclonal antibodies directed against the human T-cell-receptor subunit CD3, or approximately 30 of the known T-cell-receptor variable regions, or T-cell-receptor constant regions are available from T-cell Diagnostics (Woburn, Mass.) and/or PharMingen (San Diego, Calif.). The well studied antibody against human CD3, called OKT3, is available from Becton Dickerson (San Jose, Calif.). In fact, the unconjugated form of the OKT3 antibody has been used as an immunosuppressant in human transplant patients for the past several years.

The important triggering molecule on a T-cell is the T-cell-receptor. It has been known for many years that the analogous triggering molecule on other effector leukocytes, such as natural killer cells, monocytes, and macrophages, is the receptor for the Fc region of immunoglobulins. Antibodies to this Fc receptor (FcR, also called CD64, CD32, and CD16) can be used to redirect the killing of tumor cells by these effector cells. It is well known in the art that conjugates of anti-Fc receptor antibodies and anti-tumor antigen antibodies work exactly like conjugates of anti-T-cell-receptor antibodies and anti-tumor antigen antibodies (reviewed by Fanger, Morganelli, & Guyre [1992] *Crit. Rev. Immunol.* 12, 101–124). Thus, it is clear that folate/anti-Fc receptor conjugates can target FR positive tumor cells for lysis by natural killer cells, monocytes, and macrophages. Antibodies to the human Fc receptor are available in purified form from various vendors, including PharMingen (San Diego, Calif.).

Folate is conjugated to a suitable anti-T-cell-receptor antibody using standard techniques well known in the art (Leamon, C. P. & Low, P. S. [1992] *J Biol Chem* 267, 24966–[24971]. By way of example, folate is conjugated to an antibody using a carbodiimide procedure. Briefly, a molar excess of EDC (1-ethyl-3-[3-dimethyl-aminopropyl] carbodiimide hydrochloride) is mixed with folate dissolved in dimethyl-sulfoxide. A molar excess of the folate is then mixed with antibody. The formed conjugate is separated from the reaction mixture, typically using gradient separation techniques. A detailed description of the preparation of folate conjugated to specific anti-T-cell-receptor antibodies is set forth hereinafter in the examples.

It is known that some folate analogues also bind with high affinity to the FR (reviewed by Westerof, G. R., Jansen, G., van Emmefik, N., Kathmann, I., Rijksen, G., Jackman, A. L. & Schornagel, J. H. et al. [1991] *Cancer Research* 51, 5507–5513). These include CB3717 ($N^{10}$-propargyl-5,8-dideazafolic acid) and ICI-198,583 (2-deamino-2-methyl-$N^{10}$-propargyl-5,8-dideazafolic acid), which are available from ICI-Pharmaceuticals Division (Aidefly Park, Macclesfield, Chesire, United Kingdom). Thus, folate analogues which have high affinity for the FR but lower affinity for the reduced folate/MTX carrier will also be effective as antibody conjugates in the targeting of tumor cells that are FR positive.

Physiological conditions for binding are generally those necessary to sustain viability of the cell during binding. Those conditions are well known in the art. Typically, temperature can range from about 4° C. to about 50° C., preferably from about 15° C. to about 40° C. and, more preferably from about 25° C. to about 37° C. Typically, pH can range from about 6.0 to about 8.0, preferably from about 6.5 to about 7.5 and, more preferably from about 7.0 to about 7.4. Typically, the tumor cells and the folate/anti-T-cell-receptor antibody are suspended or dissolved in an aqueous medium. That medium can contain nutrients as necessary and a buffer to maintain pH so long as those constituents do not interfere with binding. The ionic strength of the medium can range from about 100 mOsm to about 400 mOsm, preferably from about 200 mOsm to about 350 mOsm and, more preferably, from about 275 mOsm to about 325 mOsm.

The time required for binding depends, as is well known in the art, on the concentrations of conjugate and tumor cells as well as temperature. Where the temperature is about 37° C., typically, the cells are maintained for a period of from about 10 minutes to about 24 hours, preferably from about 30 minutes to about 3 hours and, more preferably about 60 minutes.

A process of targeting tumor cells in accordance with the present invention can be used in vitro, in situ or in vivo. Where the cells are located in vitro, binding of the folate/anti-T-cell-receptor antibody occurs in a medium containing those cells. The conjugate is added to the medium before or after addition of the cells. Where targeting occurs in situ or in vivo, the conjugate is mixed in the medium perfusing the tumor cell. That medium can be an artificial medium (e.g., saline) or a naturally occuring medium such as serum, plasma or blood. Where the tumor cells are in vitro, the conjugate is typically infused into a blood vessel perfusing those cells.

II. Process of Lysing FR$^+$ Tumor Cells

In another aspect, the present invention provides a process of lysing FR$^+$ tumor cells. In accordance with that process, the tumor cells are exposed to a population of effector-cells in the presence of an effective targeting amount of an anti-T-cell-receptor or anti-Fc receptor antibody conjugated to folate and the cells are maintained for a period of time sufficient for lysis.

The population of effector-cells comprises: 1) T-cells that bind the T-cell-receptor antibody conjugated to folate or 2) natural killer cells, monocytes, and macrophages that bind the Fc receptor antibody conjugated to folate. Physiological conditions and maintenance times are the same as set forth above.

A process of the present invention has several advantages over processes using bispecific antibodies. The present method takes advantage of the high affinity of folate for the FR ($K_D$ about 1 nM) as compared to the constitutive folate carrier protein(s) ($K_D$ about 100 mM) that is expressed by most cells. A folate/anti-T-cell-receptor conjugate of the present invention binds to the FR with approximately ten-fold reduced affinity compared to free folate. Further, such conjugates mediate specific lysis of the FR$^+$ tumor cells.

Three observations regarding the effectiveness of the folate targeting approach make it particularly useful. First, all three different anti-T-cell-receptor antibodies mediated lysis with less than a ten-fold difference between them, despite the fact that these antibodies differ in affinity by at least 100-fold ($K_D$1B2 about 1 nM; $K_D$KJ16 about 100 nM; $K_D$ of 2C11 is>10 nM). Second, four different tumor cell lines with a wide range of densities of the high-affinity FR were specifically lysed while the FR-negative tumor line was spared. The latter result indicates that the ubiquitous expression of folate carrier protein by cells may not result in destruction of most normal cells. Third, the tumor cells were very effectively killed by a preparation of activated-T-cells that was taken directly from a normal individual (i.e. mouse). These T-cells are analogous to the polyclonal effector cells that can be expected to be present in most patients.

The tumor lines with similar levels of the FR are not lysed equally well. There are likely other factors that contribute to efficient recognition and lysis mediated by the folate/antibody conjugates, just as there are with conventional bispecific antibodies. These factors include adhesion molecule levels and intrinsic susceptibilities of the tumor cells.

Both the reduced size and immunogenicity of antibody/folate conjugates provide additional advantages of this approach over conventional bispecific antibodies. Folate/antibody conjugates are approximately one-half the size of bispecific antibodies. Folate/single-chain Fv regions are approximately 30 kDa compared to 60 kDa, which is currently the smallest active form of a bispecific antibody (i.e. two linked Fv regions). This reduced size likely results in improved tumor penetration and tumor/tissue localization ratios. Finally, immunogenicity is likely reduced because human anti-immunoglobulin responses to the anti-FR can not occur when folate is used directly as the targeting moiety.

III. Conjugate of Folate and an Anti-T-Cell-Receptor Antibody

The present invention further provides a conjugate of folate to an anti-T-cell-receptor antibody or other anti-effector cell antibody. A conjugate of the present invention is made in accordance with procedures set forth above. A conjugate of the present invention can comprise folate conjugated to any anti-T-cell-receptor (or other anti-effector cell) antibody. Exemplary and preferred such antibodies are set forth above. Most preferred are conjugates of folate with antibody 1B2 or the antibody produced by hybridoma KJ16 or hybridoma 2C11.

It is likely that the folate conjugates described here can be optimized further by engineering antibodies for uniform coupling of folate through the γ-carboxyl. For example, a ten-fold increase in folate/toxin effectiveness was observed when only the γ-carboxyl of folate was coupled through a disulfide bond rather than coupling both α and γ-carboxyls through carbodiimide-mediated linkages. The cloning of a single-chain 1B2 antibody has been described (Schodin, B. A. & Kranz, D. M. [1993] *J. Biol. Chem.* 268, 25722–25727). Segal and his colleagues have also described an active anti-CD3 single-chain antibody (Jost, C. R., Kurucz, I., Jacobus, C. M., Titus, J. A., Geroge, A. J. T. & Segal, D. M. [1994] *J. Biol. Chem.* 269, 26267–26273).

The following Examples illustrate preferred embodiments of the present invention and are not limiting of the claims and specification in any way.

EXAMPLE 1: Conjugates of Folate and Anti-T-Cell-Receptor Antibodies

Monoclonal antibody 1B2, a mouse IgG1 specific for the T-cell-receptor of CTL 2C, was prepared from ascites in BALB/c mice by ammonium sulfate precipitation followed by DEAE anion exchange (Kranz, D. M., Tonegawa, S. & Eisen, H. N. [1984] *Proc. Natl. Acad. Sci. USA* 81, 7922–7926). Hybridoma KJ16, a rat IgG antibody specific for the Vβ8 region of the T-cell-receptor (Haskins, K., Hannum, C., White, J., Rhoem, N., Kubo, R., Kappler, J. & Marrack, K. [1984] *J. Exp. Med.* 160, 452–471) was cultured in low serum media (1% fetal bovine serum in DME) in a bioreactor. The antibody was concentrated by ammonium sulfate precipitation. Hybridoma 2C11, a hamster IgG specific for the mouse CD3 epsilon subunit (Leo, O., Foo, M., Sachs, D. H., Samelson, L. E. & Bluestone, J. A. [1987] *Proc. Natl. Acad. Sci. USA* 84, 1374), was cultured in serum-free media and purified over a Protein G-Sepharose column. Hybridomas that secrete antibodies to MHC class I $L^d$, 30.5.7 (Ozato, K., Hansen, T. H. & Sachs, D. H. [1980] *J. Immunol.* 125, 2473–2477) and $K^dD^d$, 34.1.2s (Ozato, K., Mayer, N. M. & Sachs, D. H. [1982] *Transplantation (Baltimore)* 34, 113–118)), were cultured in the RPMI media described above and used in flow cytometry without further purification. 30.5.7 was also prepared as ascites fluid and used without further purification in some cytotoxicity assays. Fluorescein-labeled anti-IgG antibodies were obtained from Kirkegarrd and Perry, Inc.

Folate was coupled through carboxyl groups to antibody amine groups using a carbodiimide procedure similar to that previously described (Leamon, C. P. & Low, P. S. [1992] *J Biol Chem* 267, 24966–24971). A five-fold molar excess of EDC [1-Ethyl-3-(3-Dimethylaminopropyl] carbodiimide hydrochloride, Pierce) was added to folate dissolved in dimethylsulfoxide. After 30 minutes at room temperature in the dark, a 10 or 100-fold molar excess of folate was added to 0.5 to 2.0 mg of antibody in 0.1 M MOPS, pH 7.5. After one hour at room temperature, the sample was applied to a Sephadex G-25 column equilibrated in phosphate buffered saline, pH 7.0 (PBS). The excluded peak fractions were pooled and analyzed spectrophoto-metrically at 280 and 363 nm. Epitope densities of folate on antibody conjugates were determined using molar extinction coefficients ($E_M$) for folate of 6,197 (363 nm) and 25,820 (280 nm). Antibody concentrations were determined by subtracting the absorbance contribution of folate at 280 nm and using an antibody $E_M$ of 224,000. Conjugates were stored at 4° C. in the dark and retained full activity over a period of at least several months.

Mass spectra were obtained using electrospray ionization. Samples were dialyzed against 1 mM potassium phosphate buffer, pH 8.0 and concentrated to 10 to 25 pmol/ml.

The anti-clonotypic antibody 1B2 has a high affinity ($K_D$~1 nM) for the T-cell-receptor on the mouse CTL clone 2C (Schodin, B. A. & Kranz, D. M. [1993] *J. Biol. Chem.* 268, 25722–25727). 1B2 was coupled at molar ratios of 10:1 and 100:1 of folate to antibody using carbodiimide EDC. EDC-mediated linkage of folate to proteins does not affect the ability of the folate to bind to the folate receptor on the cell surface (Leamon, C. P. & Low, P. S. [1992] *J Biol Chem* 267, 24966–24971). After gel filtration, the conjugates were examined spectrophotometrically ($A_{363}/A_{280}$) to determine the number of folates per antibody molecule. The 10:1 and 100:1 ratios yielded preparations containing an average of 1.3 folates/antibody and 6.0 folates/antibody, respectively.

Figure 2:
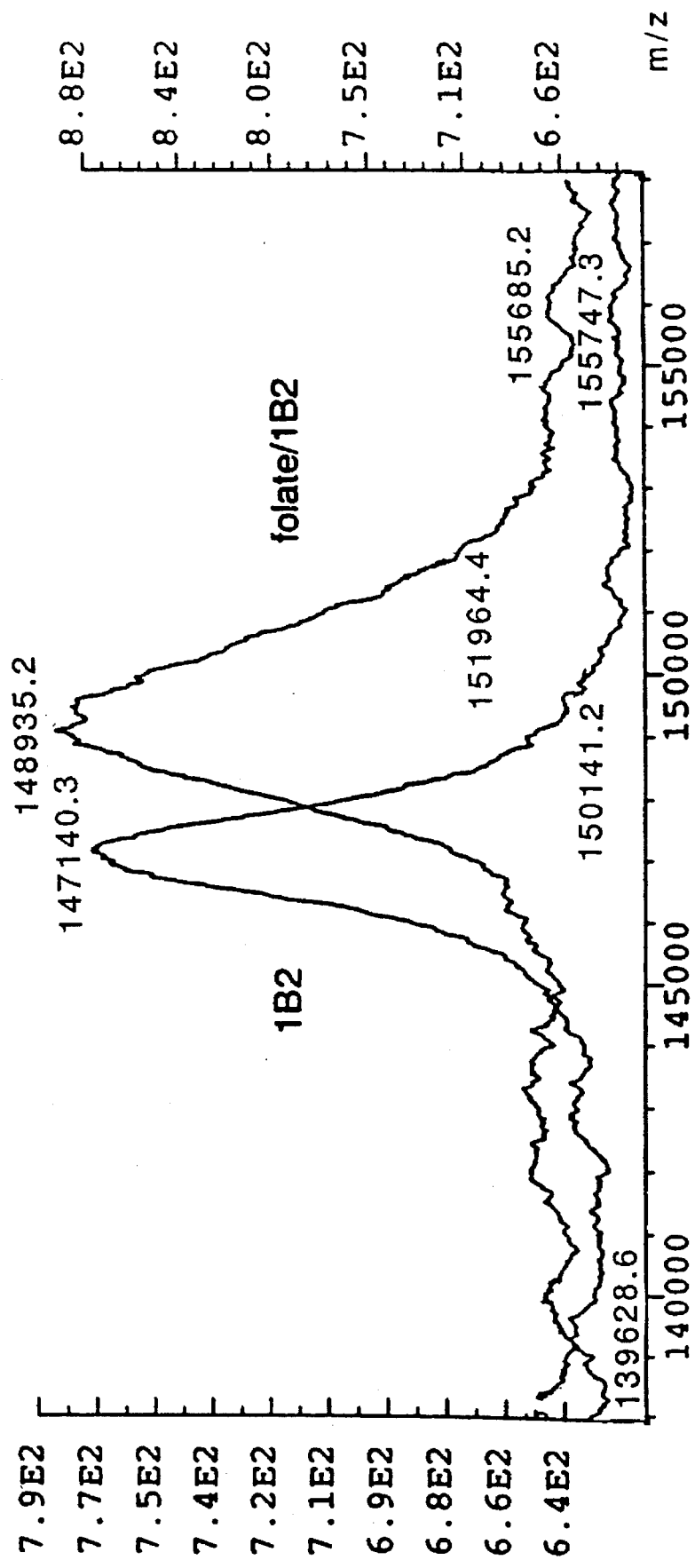
FIG. 2 shows a mass spectra of the anti-T-cell-receptor antibody 1B2 and a folate/1B2 conjugate.

The folate/1B2 conjugate (100:1) was examined by electrospray mass spectrometry. The results are shown in FIG. 2. The conjugate had an average molecular mass of 148,935 while the unlabeled 1B2 exhibited a mass of 147,140. By this estimate, the preparation contained an average of 4.1 folates/antibody. Analysis of separate H and L chain profiles yielded a value of 4.9 folates/antibody. Integration of the mass spectrometry peak indicated that>95% of the antibody molecules contained less than 10 folate molecules.

Two additional anti-T-cell-receptor antibodies, KJ16 and 2C11, were coupled with folate at the 1013:1 molar ratio of folate to antibody. These antibodies exhibit different affinities from 1B2, and they recognize T-cell-receptor epitopes on the V/β region and CD3 molecules present on mouse CYL 2C. Data from studies of such conjugates was used to ascertain whether T-cell-receptor epitope or antibody affinity affected tumor cell targeting. Each of these preparations exhibited folate densities that were similar to 1B2 (4.9 for KJ16 and 4.4 for 2C11).

EXAMPLE 2: Binding Studies

The following DBA/2-derived tumor cell lines were maintained in RPMI 1640 containing 5 mM HEPES, 10% fetal bovine serum, 1.3 mM L-glutamine, 50 mM 2-ME, penicillin, and streptomycin: Mel, murine erythroleukemia cell; La, a subline of Mel that has been selected on low folate (Brigle, K. E., Spinella, M. J., Westin, E. H. & Goldman, I. D. [1994] *Blochem Pharmacol* 47, 337–345); L1210, a leukemia cell line; LL3, a subline of L1210 selected on low 5-formyltetrahydro-folate as previously described (Brigle, K. E., Westin, E. H., Houghton, M. T. & Goldman, I. D. [1991] *J Biol Chem* 266, 17243–17249), and F2-MTX$^r$A, a subline selected for resistance to methotrexate by virtue of impaired transport (Brigle, K. E., Seither, R. L., Westin, E. H. & Goldman, I. D. [1994] *J Biol Chem* 269, 4267–4272). La and LL3 cells express the α-form of the folate receptor; F2-MTX$^r$A cells express the β-form of the folate receptor. CTL clone 2C, a mouse alloreactive cell line specific for $L^d$, was maintained in the same RPMI media with 10% supernatant from concanavalin A-stimulated rat spleen cells, 5% α-methyl mannoside, and mitomycin c treated BALB/c spleen cells as stimulators (Kranz, D. M., Sherman, D. H., Sitkovsky, M. V., Pastemack, M. S. & Eisen, H. N. [1984] *Proc. Natl. Acad. Sci. USA* 81, 573–577).

Binding assays were conducted using $^{125}$I-folate (about 2200 Ci/mmol). Cells were washed with phosphate buffered saline (PBS) with 0.1% bovine serum albumin (BSA), pH 7.4 (PBS-BSA), to remove excess free folate present in the cell culture medium. Cells, labeled folate, and competitors were incubated in 75 ml PBS-BSA for one hour at 37° C. Bound and free ligand were separated by centrifugation through oil (80% dibutyl phthalate-20% olive oil) at 12,000×g for 3 sec. Tubes were frozen in an ethanol-dry ice slurry; the frozen tubes were cut and the pelleted cells and supernatants were counted separately. Binding parameters were calculated using nonlinear regression analysis.

Because cytotoxicity assays were performed at 37° C., all binding studies were also done at 37° C. The affinity of $^{125}$I-folate for the FRα and FRβ isoforms of the receptor was determined using the FRα+ and FRβ$^+$ lines, La and F2-MTX$^r$A. At 0° C., $K_D$ values were 0.9 nM and 0.7 nM, respectively, using free folate as inhibitor and non-linear analysis of the saturation binding curves. At 37° C., $K_D$ values were determined to be 1 and 5 nM for La and F2-MTX$^r$A, respectively (FIG. 3A).

Figure 3A:
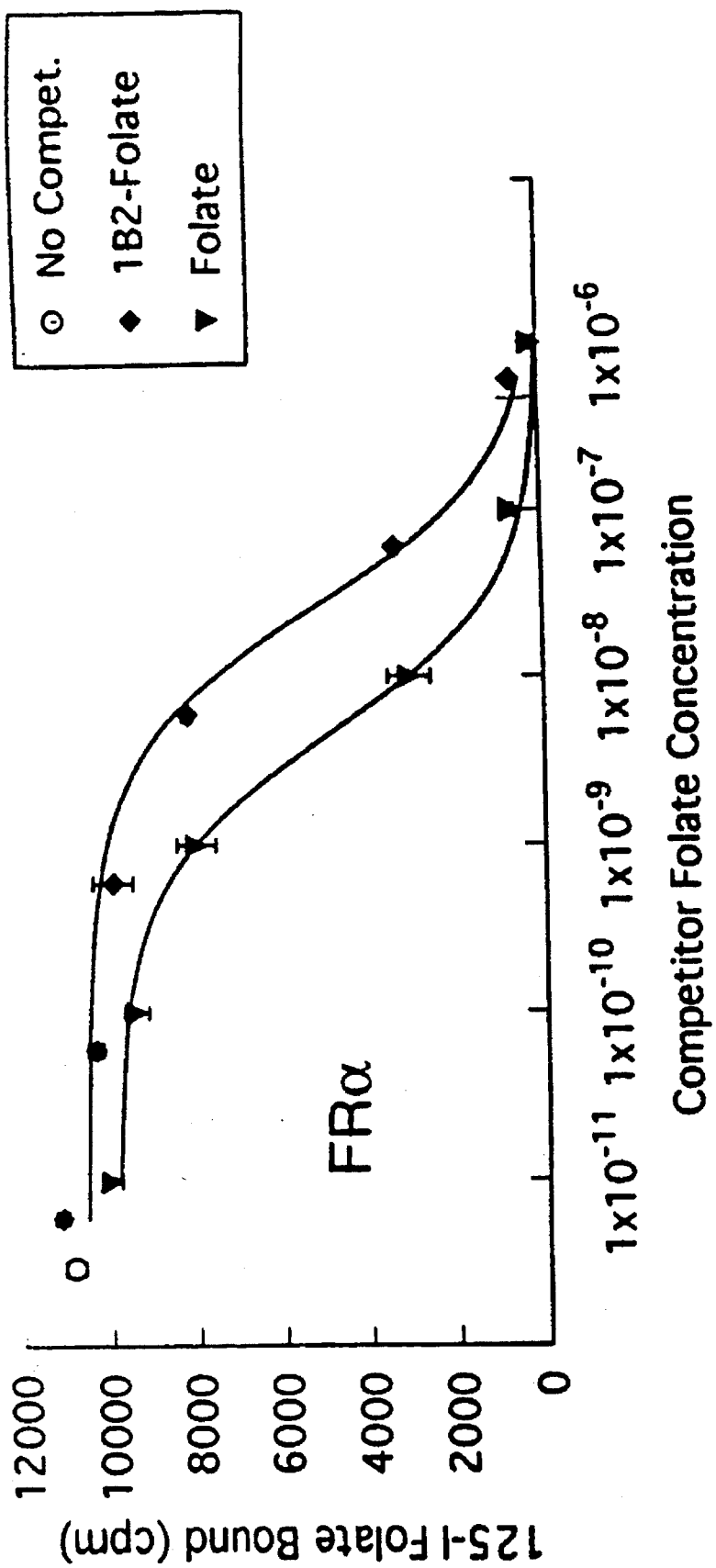
FIG. 3A shows an inhibition binding curve of free folate and folate/antibody conjugates to La cells, which express FR$\alpha$.
Figure 3B:
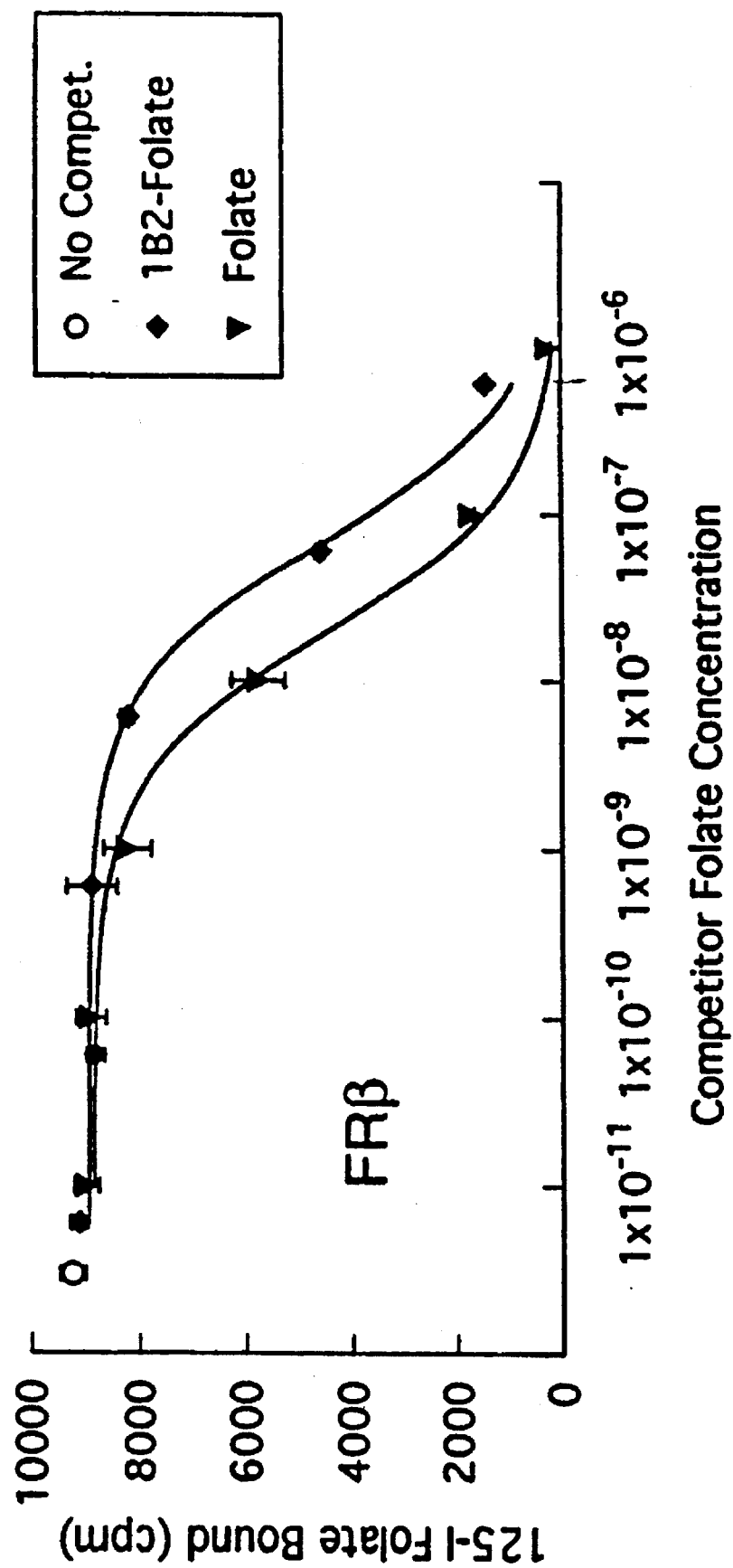
FIG. 3B shows an inhibition binding curve of free folate and folate/antibody conjugates to F2-MTX$^r$A cells, which express FR$\beta$.

A competition experiment was performed with both cell lines using folate/1B2 (100:1), folate/1B2 (10:1), and unlabeled 1B2 (see FIGS. 3A and 3B). Both conjugates, but not the unlabeled 1B2, inhibited the binding of the labeled ligand. Folate in conjugate form was about 10-fold less effective at binding than free folate. The average $K_D$ of the folate/1B2 preparation for the two cell lines was determined to be 20 nM and 60 nM for FRα and FRβ, respectively.

Figure 4:
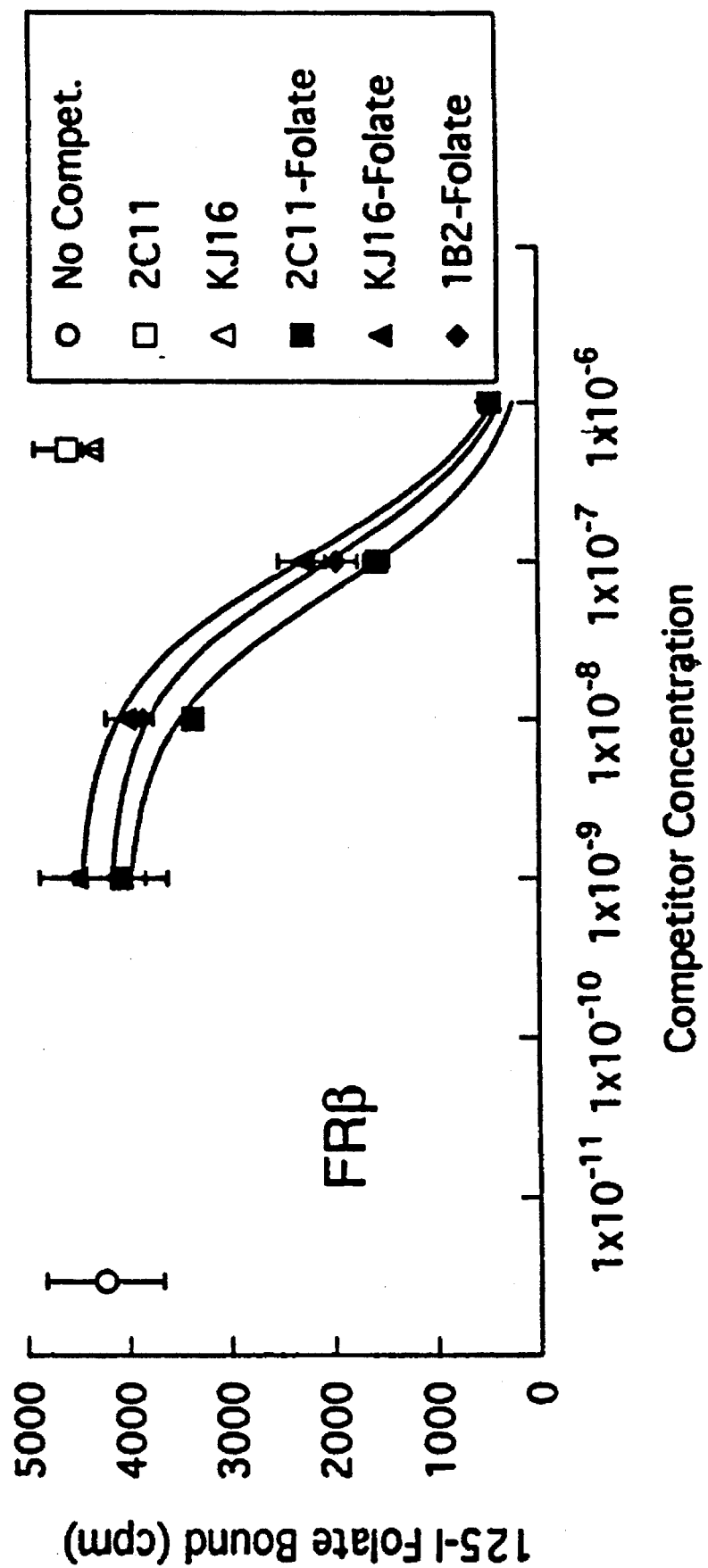
FIG. 4 shows inhibition binding curves of conjugates of folate and three anti-T-cell-receptor antibodies to F2-MTX$^r$A cells (FR$\beta$).

A comparison of the three different folate/anti-T-cell-receptor antibody conjugates is shown in FIG. 4. All three conjugates inhibited the binding of $^{125}$I-folate to FRβ$^+$ cells. Inhibition was not observed with unlabeled antibodies. The calculated $K_D$ of the 1B2, KJ16, and 2C11 conjugates were 80 nM, 90 nM, and 50 nM, respectively. These similarities indicated that significant differences in the targeting effectiveness of these antibodies likely depends on factors other than their folate density.

EXAMPLE 3: Cytotoxicity of Monoclonal Antibody Folate/1B2 Conjugates with a Cloned Cytotoxic T-cell Line as Effector Five different mouse tumor cell lines (see Table 1, below) were examined in a $^{51}$Cr-release assay with the mouse CTL clone 2C and conjugates of the anti-T-cell-receptor antibody 1B2 and folate. Each of these lines were also examined for binding by $^{125}$I-folate to approximate the number of FR at 37° C.

Figure 5:
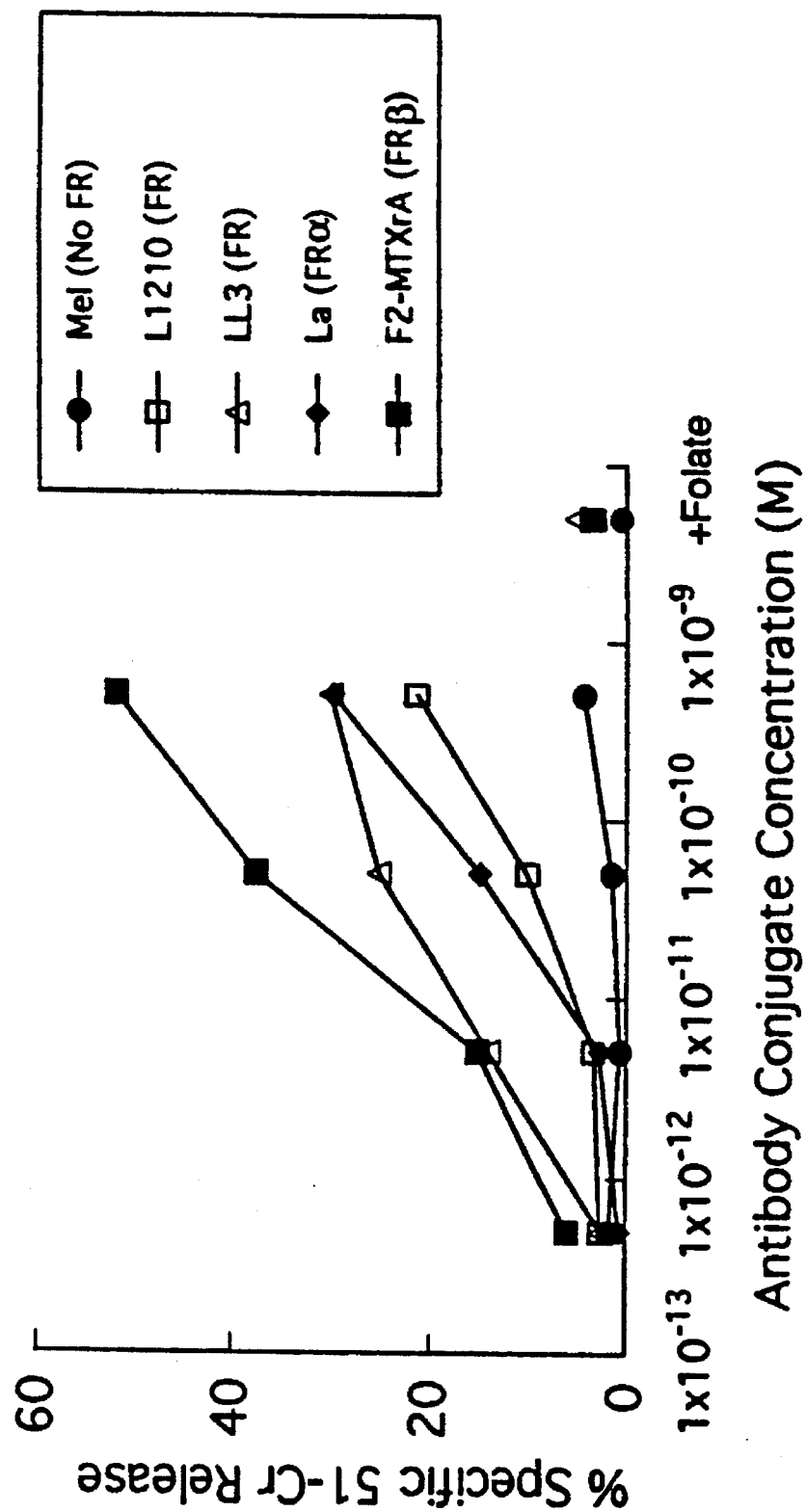
FIG. 5 shows cytotoxicity assays of various tumor cell lines with folate/anti-T-cell-receptor antibody 1B2 and CTL clone 2C.

1B2/folate conjugate (see FIG. 5). The lysis was completely inhibited by free folate indicating that it was mediated by binding to the FR and not by other cell surface molecules (e.g. Fc receptors). The extent of lysis was correlated with the level of surface FR with the F2-MTX$^r$A line always exhibiting more lysis than the other lines. In contrast, the FR$^-$ cell line Mel was not lysed even at a 1B2/folate concentration that was 1000 times higher than the concentration required for detectable killing of the FR$^+$ line F2-MTX$^r$A.

Figure 6A:
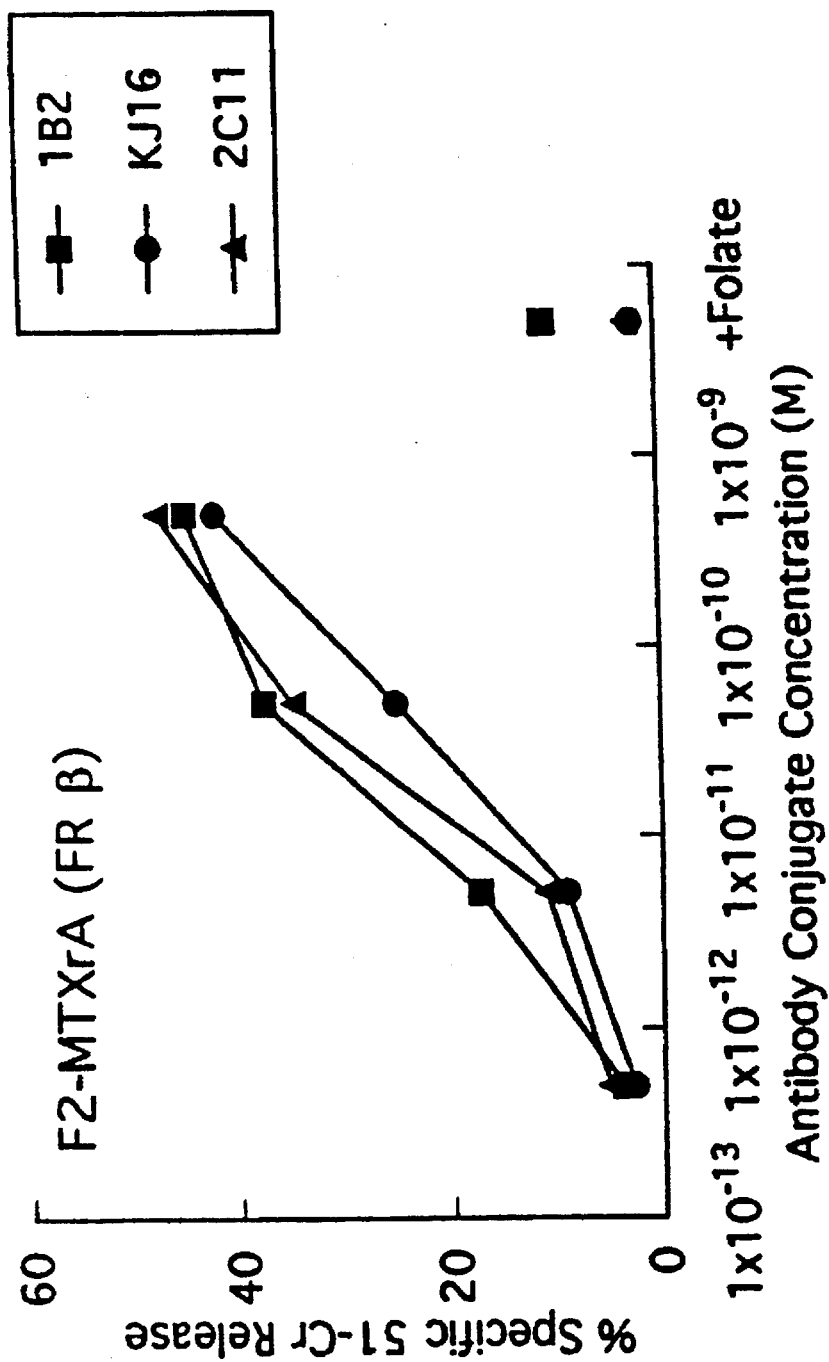
FIG. 6A shows a cytotoxicity assay of an FR$^+$ tumor cell line (F2-MTX$^r$A) with three different folate/anti-T-cell-receptor conjugates and CTL clone 2C.
Figure 6B:
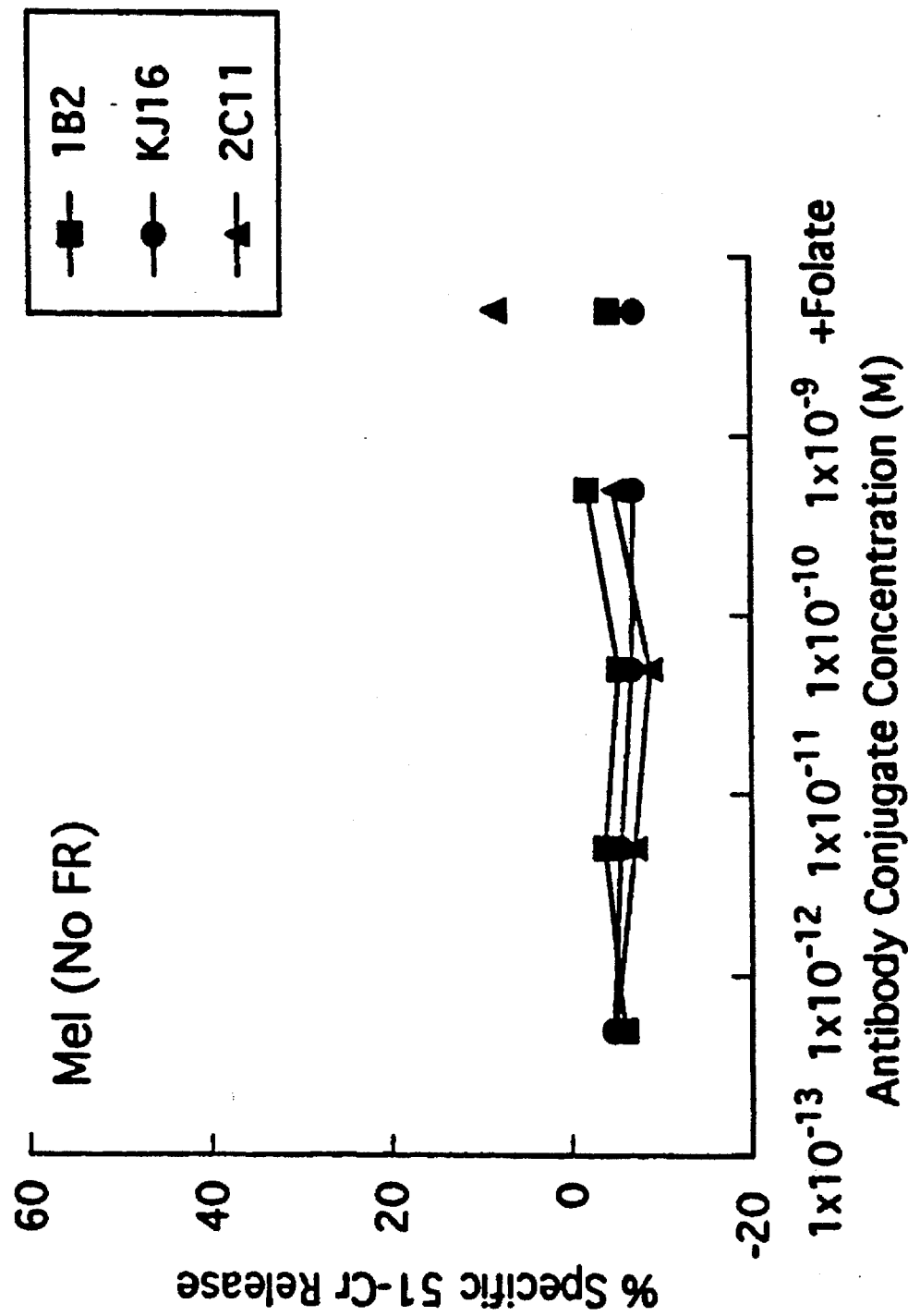
FIG. 6B shows a cytotoxicity assay of an FR$^-$ tumor cell line (Mel) with three different folate/anti-T-cell-receptor conjugates and CTL clone 2C.

EXAMPLE 4: Cytotoxicity of Monoclonal Antibody Folate/KJ16 Conjugates with a Cloned Cytotoxic T-cell Line as Effector To determine if a different folate/anti-T-cell-receptor antibody conjugate was effective at mediating specific lysis, the FR$^+$ cell line F2-MTX$^r$A, and the FR$^-$ cell line, Mel, were assayed at various KJ16/folate conjugate concentrations with the effector cell 2C. The KJ16 antibody recognizes the variable region of the T-cell-receptor and is analogous to many of the anti-human TCR antibodies available from T-cell Diagnostics and PharMinogen. The conjugate mediated lysis of F2-MTX$^r$A (see FIG. 6A) but not the parental line, Mel (see FIG. 6B). The lysis was specific as indicated

| Cell Line | FR Type | Bmax[a] (sites/ce II) | Kd (nM) 0* | Kd (nM) 37* | Class I[c] (mean floures. units) L[d] | Class I[c] (mean floures. units) (K[d]D[d]) | Class I[c] (mean floures. units) No Ab |
|---|---|---|---|---|---|---|---|
| F2-MTXrA | β | 200,000 | 0.7 | 5 | 131 | 174 | 4 |
| La | α | 60,000 | 0.9 | 1 | 64 | 76 | 4 |
| LL3 | α | 20,000 | 0.3 | ND | 144 | 183 | 5 |
| L1210 | not determined | 8,000[b] | ND | ND | 125 | 154 | 3 |
| Mel | no detecable FR | <4,000[b] | ND | ND | 61 | 79 | 4 |

As expected, the highest levels of expression were detected for the low folate-selected lines F2-MTX$^r$A, La, and LL3. The DBA-derived leukemia parental line L1210 had a low but detectable level of FR and the parental line Mel had no detectable FR.

For this example and those shown below, tumor cells were labeled with 50 μl $^{51}$Cr (2.5 mCi/ml) for 60 minutes at 37° C., washed twice with folate-free RPMI containing 5% fetal calf serum (folate-free media), and used in 96-well plate cytotoxicity assays at $10^4$ cells per well. Antibodies and folate/antibody conjugates were added to wells at various concentrations diluted in folate-free media. For folate inhibition studies, folate was added at a final concentration of 2.5 mM. Effector cells (2C or SEB-reactive polyclonal BALB/c T-cells) were added at effector to target cell ratios ranging from 5:1 to 15:1. For experiments with 2C as effector cells, the anti-L$^d$ antibody was used at a 1:100 dilution of ascites to inhibit recognition of the L$^d$ alloantigen by CTL 2C. Plates were incubated at 37° C. for 4 hours and supernatants were removed for gamma counting. Specific $^{51}$Cr release was determined by:

% Specific $^{51}$Cr release=[(experimental counts—spontaneous counts)/(maximal counts—spontaneous counts)]X 100. Assays were performed in triplicate. The specific release mediated by the folate conjugates were determined by subtracting the release in the absence of the conjugates.

Because each of the tumor cell lines express the alloantigen L$^d$ that is recognized by CTL clone 2C, assays were performed in the presence of excess monoclonal anti-L$^d$ antibody to minimize non-FR mediated lysis. Lysis of each of the FR$^+$ cell lines was detected in the presence of the by the ability of free folate to inhibit lysis by each of the conjugates.

EXAMPLE 5: Cytotoxicity of Monoclonal Antibody Folate/2C11 Conjugates with a Cloned Cytotoxic T-cell Line as Effector To determine if yet a different folate/anti-T-cell-receptor antibody conjugate was effective at mediating specific lysis, the FR$^+$ cell line F2-MT$^r$A, and the FR$^-$ cell line, Mel, were assayed at various 2C11/folate conjugate concentrations with the effector cell 2C. The 2C11 antibody recognizes the CD3$_ε$ subunit of the T-cell-receptor and is analogous to the anti-human TCR antibody OKT3 which has been used as an immunosuppressant in human transplant patients. The 2C11 and OKT3 antibodies have also been used extensively in the construction, testing, and in vivo studies of bispecific antibodies. The 2C11/folate conjugate mediated lysis of F2-MTX$^r$A (see FIG. 6A) but not the parental line, Mel (see FIG. 6B). The lysis was specific as indicated by the ability of free folate to inhibit lysis by each of the conjugates.

EXAMPLE 6: Cytotoxicity of Monoclonal Antibody Folate/KJ16 Conjugates with Polyclonal T-cells as Effectors In order to show that the conjugates described above are capable of mediating lysis by various effector cells, a polyclonal population of T-cells was obtained from a normal BALB/c mouse. These effector cells were tested with conjugates of folate and the anti-variable region antibody KJ16. Activated T-cells from a BALB/c mouse were obtained using standard procedures by in vitro stimulation of spleen cells with SEB (Soo Hoo, W. F. & Kranz, D. M. [1993] J. Immunol. 150, 4331–4337). Briefly, spleen cells were stimulated by incubation of 5 million cells/ml with 10 μg/ml Staphylococcal enterotoxin B (Toxin Technologies, Madison, Wis.), 10% supernatant from concanavalin A-stimulated rat spleen cells, and 5% α-methyl mannoside. Cells were used 3 or 4 days after stimulation. This T-cell population is enriched for Vβ8⁺/KJ16-reactive cells although they do not express the epitope of the clonotypic antibody 1B2.

Figure 7A:
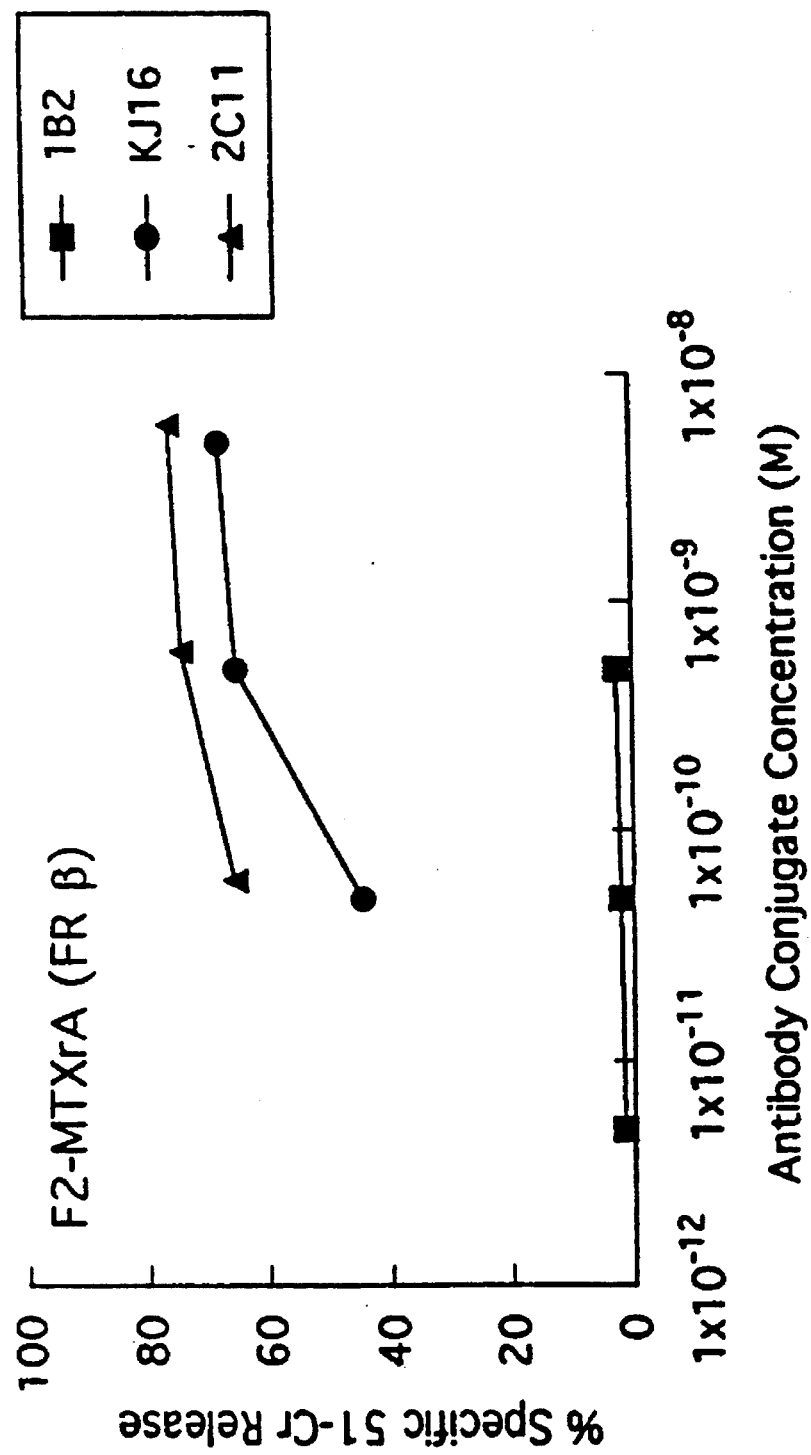
FIG. 7A shows a cytotoxicity assay of an FR$^+$ tumor cell line (F2-MTX$^r$A) with three different folate/anti-T-cell-receptor conjugates and polyclonal BALB/c T-cells.
Figure 7B:
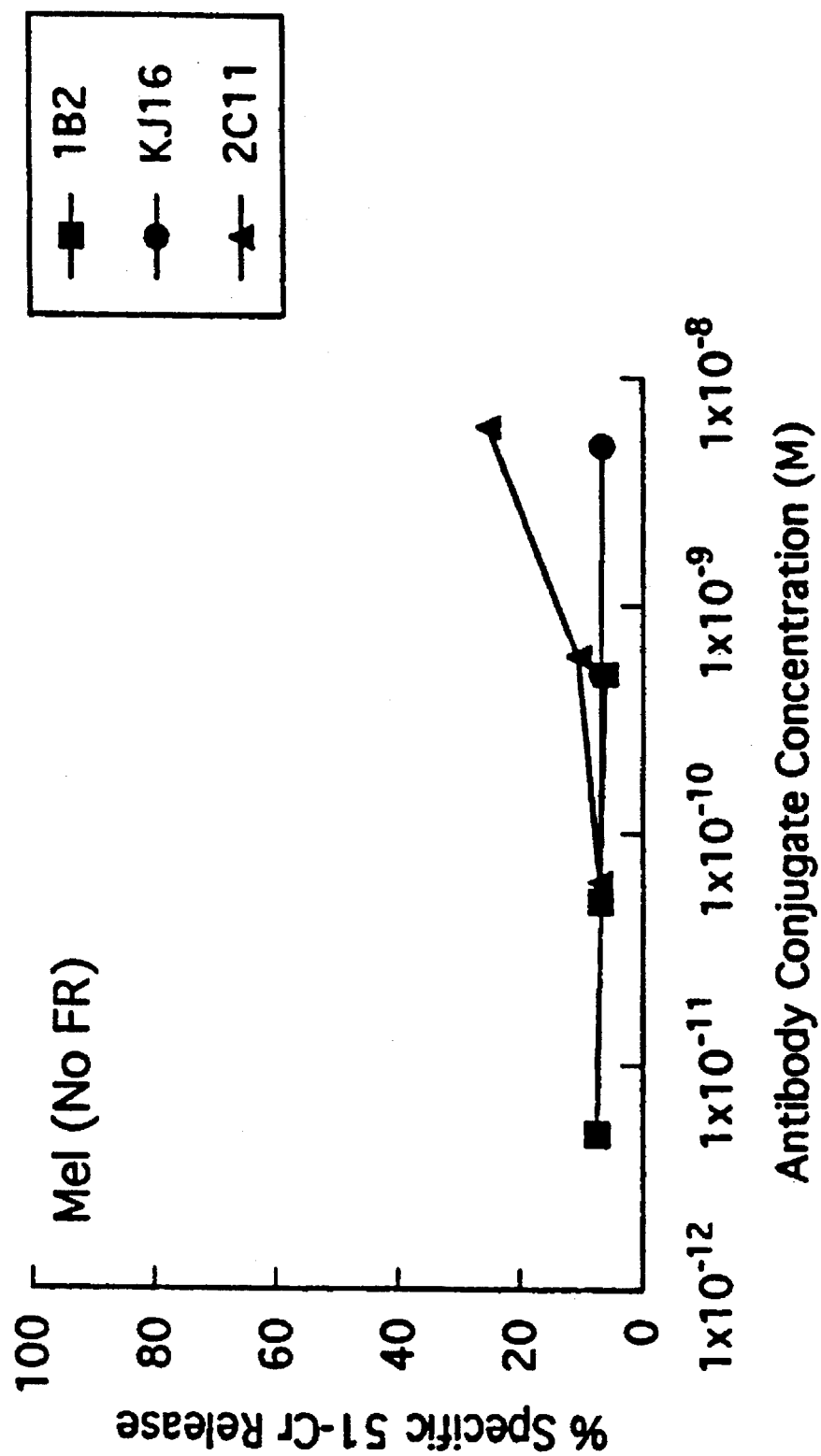
FIG. 7B shows a cytotoxicity assay of an FR$^-$ tumor cell line (Mel) with three different folate/anti-T-cell-receptor conjugates and polyclonal BALB/c T-cells.

The FR⁺ F2-MTX$^r$A cell line was efficiently lysed by the BALB/c-derived T-cells in the presence of the folate/KJ16. As expected, lysis was not observed with the folate/1B2 conjugate (see FIG. 7A). In a separate experiment with polyclonal CTL, folate/KJ16 mediated lysis was shown to be completely inhibited by free folate. In contrast, there was relatively little effect on the FR⁻ cell line, Mel (see FIG. 7B).

EXAMPLE 7: Cytotoxicity of Monoclonal Antibody Folate/2C11 Conjugates with Polyclonal T-cells as Effectors The polyclonal effector cells described in Example 6 were also tested with conjugates of folate and the anti-CD3 antibody 2C11. Again, the FR⁺ F2-MTX$^r$A cell line was efficiently lysed by the BALB/c-derived T-cells in the presence of the folate/2C11 (see FIG. 7A). In a separate experiment with polyclonal CTL, folate/2C11 mediated lysis was shown to be completely inhibited by free folate. In contrast, there was relatively little effect on the FR⁻ cell line, Mel, although at the highest concentration of 2C11 there was some lysis (see FIG. 6B).

What is claimed is:

1. A process of targeting a folate-receptor-positive tumor cell for lysis comprising binding to the tumor cell an effective targeting amount of a conjugate of an anti-T-cell-receptor antibody and folate or an analogue of folate having high affinity for the folate receptor, wherein the folate-receptor-positive tumor cell is a folate- receptor-α-positive tumor cell or a folate-receptor-β-positive tumor cell.

2. The process of claim 1 wherein binding is accomplished by exposing the tumor cell to the conjugate and maintaining the cell under physiological conditions and for a period of time sufficient for the conjugate to bind to the cell.

3. The process of claim 1 wherein the anti-T-cell-receptor antibody is a monoclonal antibody.

4. A process of lysing a folate-receptor-α-or β-positive tumor cell comprising exposing the tumor cell to a population of T-cells in the presence of an effective targeting amount of a conjugate of an anti-T-cell-receptor antibody and folate or an analogue of folate having high affinity for the folate receptor and maintaining the cells for a period of time sufficient for lysis.

5. A conjugate of an anti-T-cell-receptor antibody and folate or an analogue of folate having high affinity for an α- or β-folate receptor.

6. The conjugate of claim 5 wherein the antibody is a monoclonal antibody.

* * * * *

UNITED STATES PATENT AND TRADEMARK OFFICE
CERTIFICATE OF CORRECTION

PATENT NO.: 5,547,668

DATED : 08/20/96

INVENTOR(S): Kranz et al.

It is hereby certified that error appear(s) in the above-identified patent and that said Letters Patent is hereby corrected as shown below:

Please add a funding acknowledgment as follows:

> This invention has been supported by U.S. Army Medical Research Acquisition Activity Grant No. DAMD 17-94-J-4347

Signed and Sealed this

Sixth Day of June, 2000

*Attest:*

Q. TODD DICKINSON

*Attesting Officer*      *Director of Patents and Trademarks*